United States Patent

Beraud

(10) Patent No.: US 6,843,144 B2
(45) Date of Patent: Jan. 18, 2005

(54) DEVICE FOR EXPOSING A SAMPLE TO ELECTROMAGNETIC RADIATION, FOR TESTING THE AGING OF SAMPLES

(76) Inventor: Michel Beraud, 90, Rue Cuvier, F-83150 Bandol (FR)

( * ) Notice: Subject to any disclaimer, the term of this patent is extended or adjusted under 35 U.S.C. 154(b) by 41 days.

(21) Appl. No.: 10/149,872

(22) PCT Filed: Dec. 13, 2000

(86) PCT No.: PCT/FR00/03499
§ 371 (c)(1),
(2), (4) Date: Jun. 13, 2002

(87) PCT Pub. No.: WO01/44787

PCT Pub. Date: Jun. 21, 2001

(65) Prior Publication Data

US 2002/0189377 A1 Dec. 19, 2002

(30) Foreign Application Priority Data

Dec. 13, 1999 (FR) .......................................... 99 16038

(51) Int. Cl.[7] .............................................. G01N 17/00
(52) U.S. Cl. ...................................................... 73/865.6
(58) Field of Search ........................ 73/865.6; 250/372; 374/45, 57

(56) References Cited

FOREIGN PATENT DOCUMENTS

| FR | 2826118 | * 12/2002 | .......... G01N/17/00 |
| WO | WO 03/016876 A1 | * 2/2003 | .......... G01N/17/00 |

* cited by examiner

*Primary Examiner*—Thomas P. Noland
(74) *Attorney, Agent, or Firm*—Allen, Dyer, Doppelt, Milbrath & Gilchrist, P.A.

(57) ABSTRACT

A device for exposing samples to radiation to test their ageing includes a chamber having a sample-holder cage rotating about an axis, and a lamp holder for placing at least one electromagnetic radiation lamp in a fixed position in a central part of the cage and for supplying the lamp with power. An air circulation system provides a swirling air flow about the axis of the cage. The swirling air flow has components that are tangential and/or radial to the periphery of the cage, and an axial component in the central part of the cage. The cage is mounted rotationally on an axially hollowed-out hub so that the air flow is discharged through the hub. Air inlet louvers are positioned on the periphery of the cage and are directed non-radially. The device is designed to operate with the axis of the rotary cage being positioned in a horizontal direction.

30 Claims, 5 Drawing Sheets

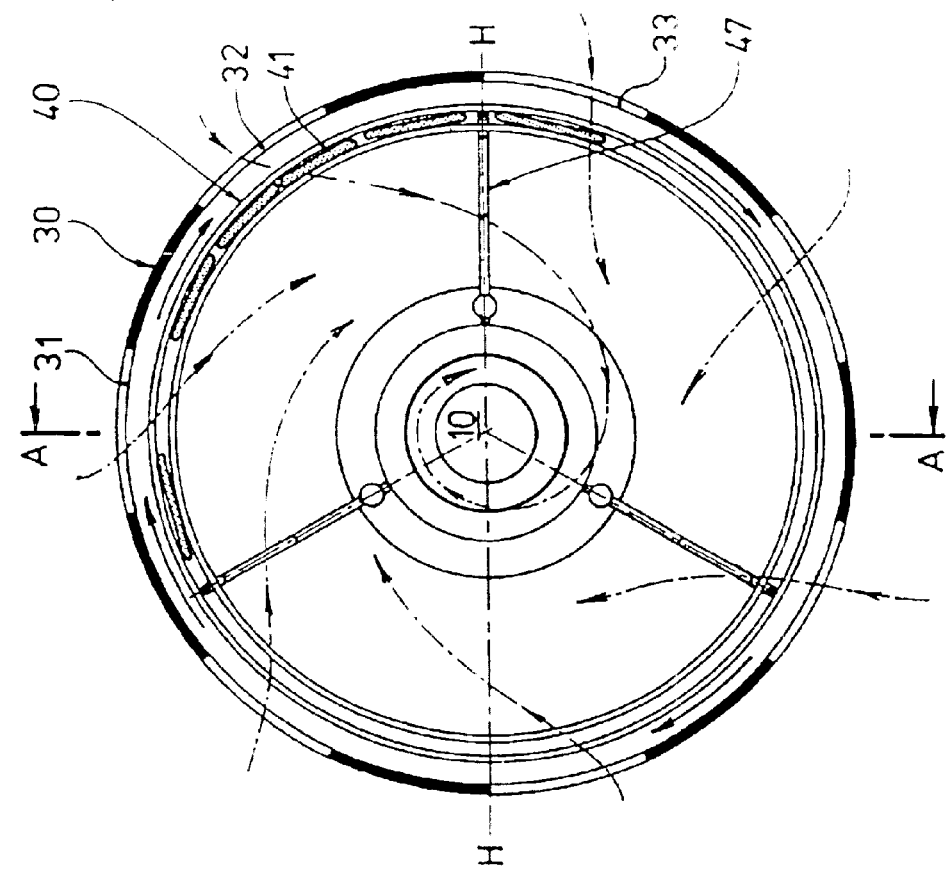
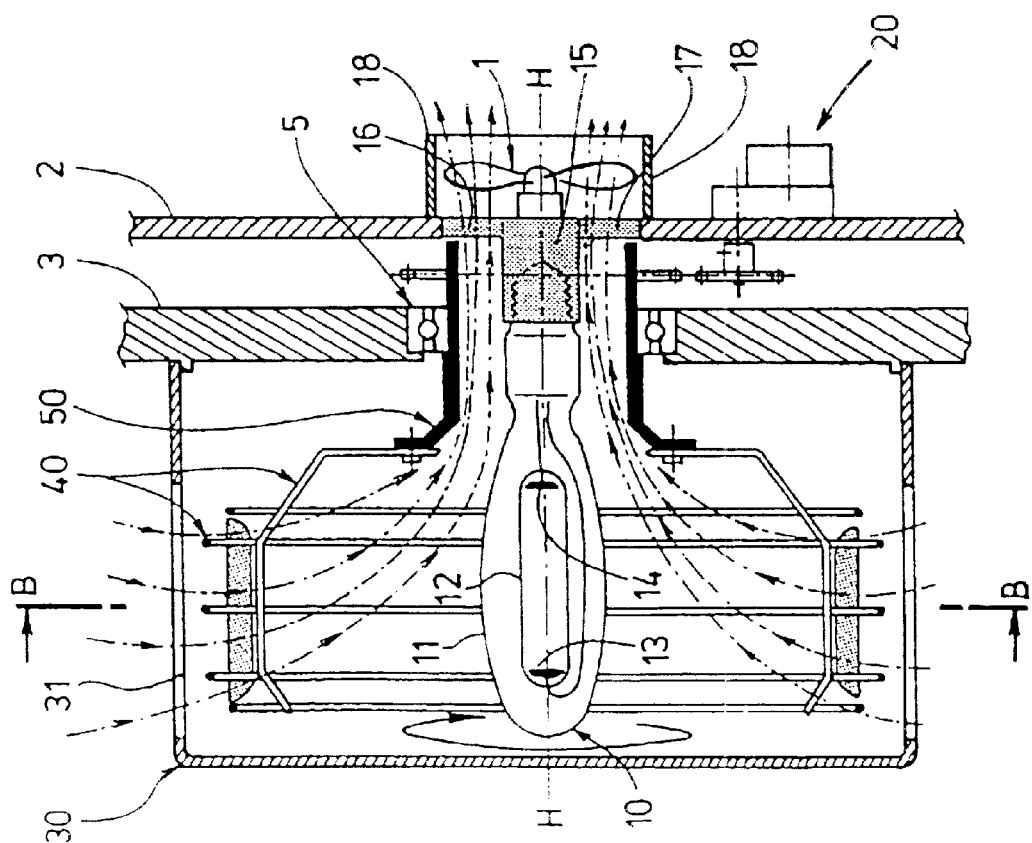
Fig.1A
Fig.1B

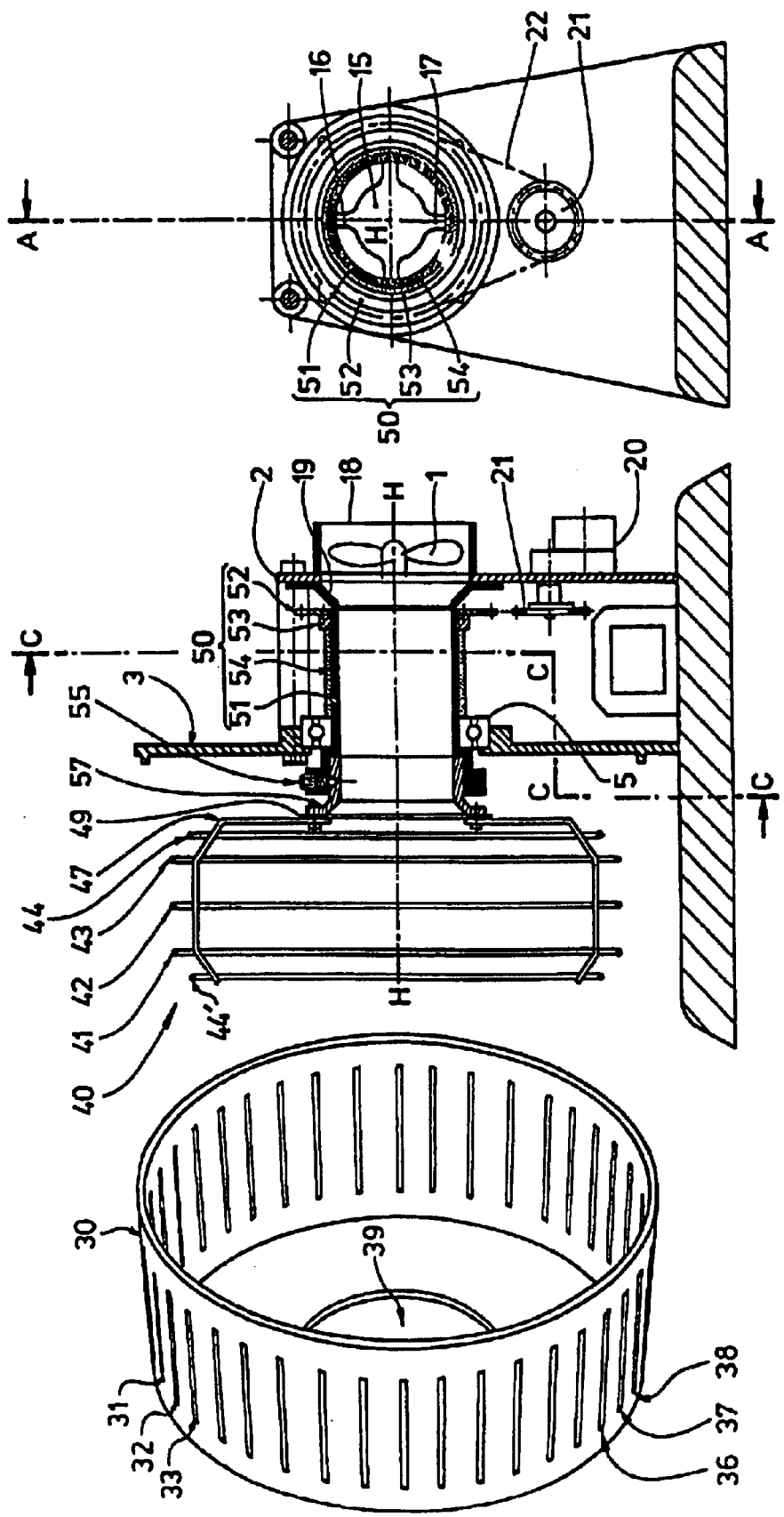

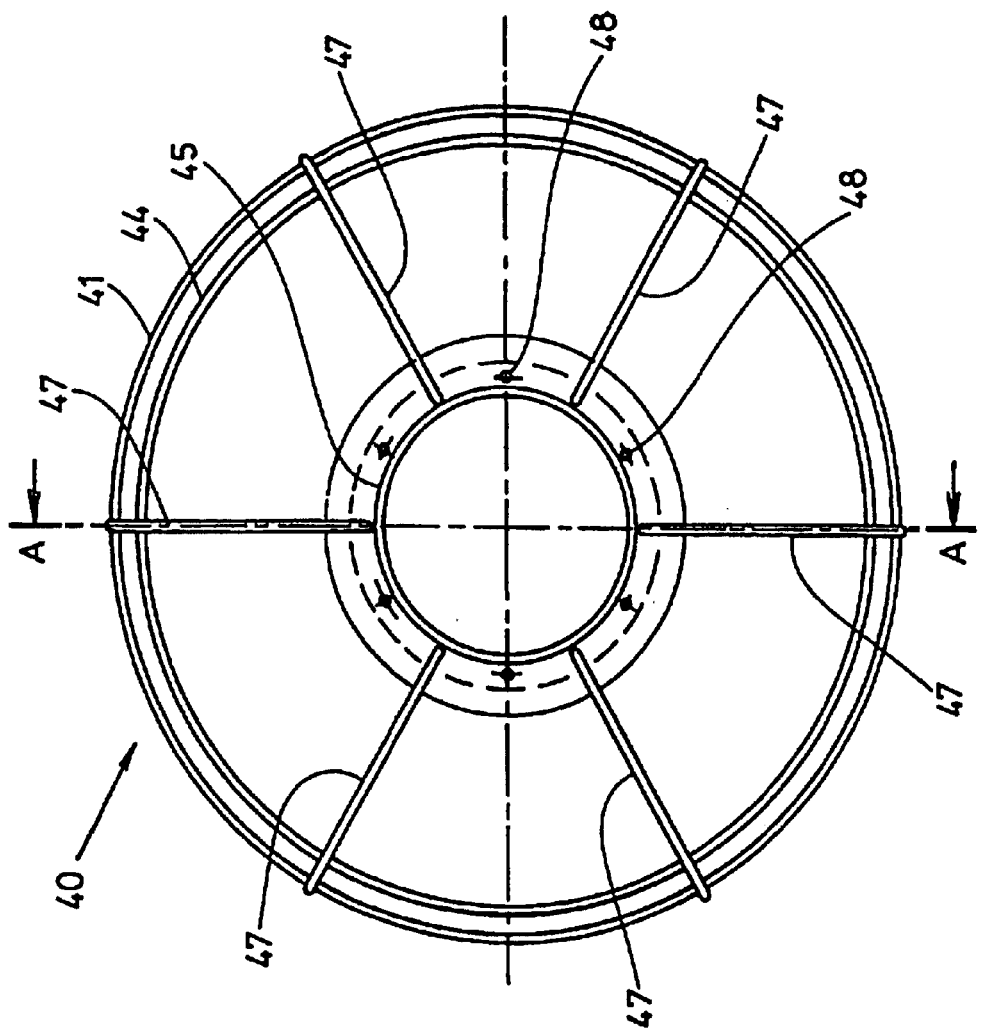
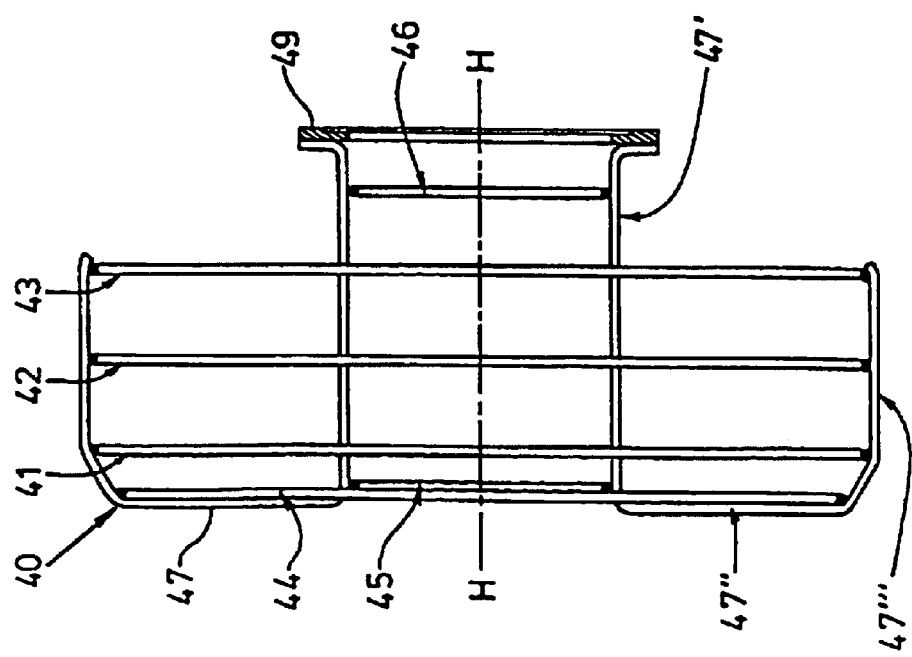
Fig. 4B
Fig. 4A

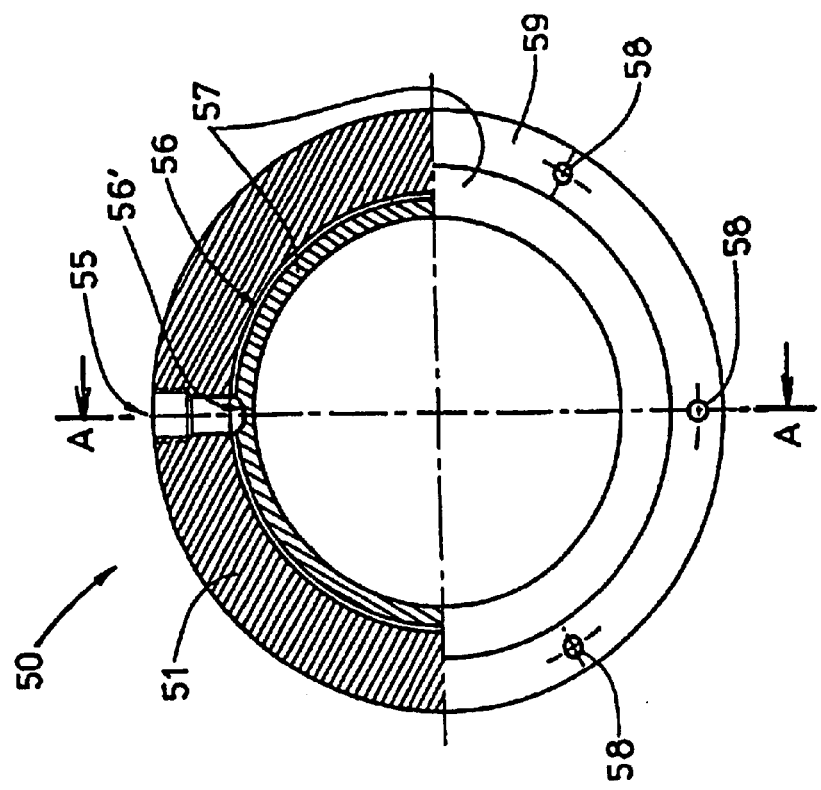
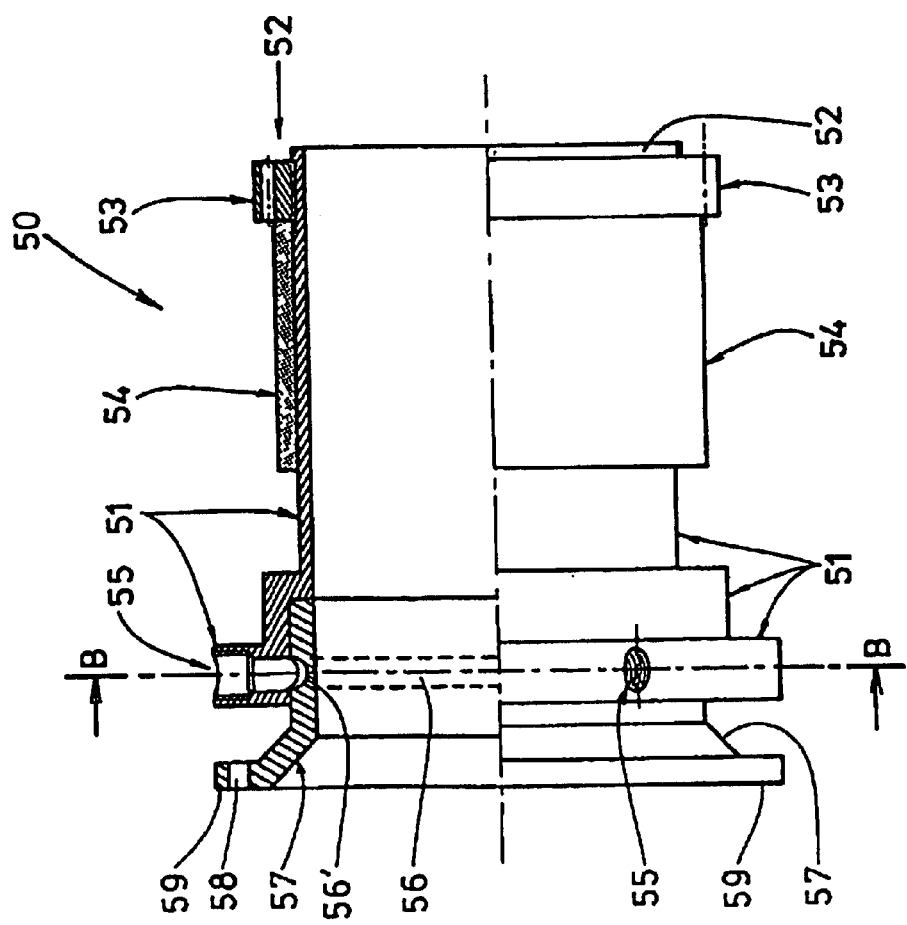

DEVICE FOR EXPOSING A SAMPLE TO ELECTROMAGNETIC RADIATION, FOR TESTING THE AGING OF SAMPLES

FIELD OF THE INVENTION

The present invention relates to the field of devices and instruments with electromagnetic radiation sources for testing the accelerated ageing of samples under the effect of light, as well as other atmospheric conditions such as temperature, humidity and water precipitation. The tests relate especially to the behavior of samples made of polymer materials which are sensitive to ultraviolet radiation.

BACKGROUND OF THE INVENTION

The natural ageing of materials under sunlight is simulated in a known way by exposing samples to a source of electromagnetic radiation whose spectral distribution has to be carefully chosen to obtain accelerated ageing that can be correlated with the ageing observed under natural conditions. There are known devices comprising a fixed bank of low-pressure arc tube lights that provide ultraviolet radiation. This bank of parallel tubes is positioned so that it faces the samples to be tested.

The drawback of the radiation from low-pressure arc tubes is that there is a low emission and an ultraviolet spectrum that is very different from a solar spectrum. This makes the tests faulty. Another drawback is that these devices cannot be used to provide an even exposure of the samples. This is to the point where the test results have poor reproducibility.

There are known devices using xenon arc lamps whose value is that they have a spectrum very close to the solar spectrum when they are appropriately filtered. With recent developments in this technique, it is now possible to adopt filtered medium-pressure mercury vapor lamps whose spectrum is very rich in ultraviolet rays and shows a high equilibrium between the longer-wavelength U.V.A. type ultraviolet rays and the shorter-wavelength U.V.S. type ultraviolet rays. This enables an efficient reproduction of the ageing process caused by sunlight.

There are known instruments for carrying out ageing tests in which the samples are mounted on a vertical, cylindrical sample-holder rotating around vertically positioned tubular xenon arc lamps. The rotation of the samples about the xenon lamps provides for even exposure to radiation. However, these lamps release a lot of heat and it is necessary to plan for an open-circuit or a closed-circuit air circulation to maintain the samples at a controlled temperature.

These instruments have the drawback of exposing the samples to varying temperatures. Indeed, the ventilation circuit has an air suction zone above the cylindrical sample-holder that prompts a vertical air flow as in a chimney stack. The air flow is heated while moving vertically along the lamps and the samples, so that the samples positioned at the top of the sample-holder are at a temperature greater than that of the samples positioned at the bottom. Identical samples located at different heights are therefore subjected to different temperatures. This again affects the reproducibility of the tests. In practice, certain users are forced to interrupt the tests to switch the positions of the samples being tested, between the top and the bottom of the sample-holder.

Devices are also known with a parallelepiped-shaped test chamber having mercury lamps positioned vertically at the four corners of the chamber, along a small, rotating sample-holding cylinder placed at the center of the chamber. The lamps and the external face of the samples are cooled by ventilated air circulation with air inlets opened in the side walls of the chamber, and an air outlet capping the entire sample-holding cylinder at the top of the chamber.

One drawback of this device is that it takes up far too much space in relation to the small surface area of the samples that can be tested in it. This device also has the drawback of showing major losses of light energy, since more than 75 percent of the light is not sent directly to the sample-holder. This device therefore has low efficiency when the depreciation cost of the equipment added to the energy expenditure is related to the surface area of the samples being tested. This adversely affects the cost of the tests.

There also exist instruments comprising a rectangular test chamber in which there is mounted a cylindrical sample-holder cage mounted rotationally on a solid driving shaft. A laminar air flow travels along the samples, propagating vertically between apertures made in the axis of the generatrix lines of the cylinder at the floor and at the ceiling of the chamber to isolate the samples from the flow of hot air coming from the lamp and to provide common testing temperatures.

Despite the laminar air flow, this instrument still has the drawback of exposing the samples to different temperatures, as the laminar air flow becomes further heated when in contact with the samples exposed to a strong light radiation. In practice, the samples placed at the top of the cage are thus exposed to a temperature several degrees higher than that of the samples placed at the bottom of the cage.

European Patent No. 320,209 describes an atmospheric test cabinet or cubicle comprising a sample holder rack rotating about a xenon light tube positioned vertically. The samples are cooled by a laminar air flow that travels vertically along the internal walls of the samples positioned along the straight sides of the rack. For reasons of economy, the air flow has a limited flow rate. This test cubicle having a vertical laminar air flow and a low flow rate has the drawback of not providing for the efficient cooling of the samples and of inducing temperature differences between the samples placed at the bottom and those placed at the top of the rack.

U.S. Pat. No. 4,760,748 describes another instrument for the testing of accelerated ageing also comprising a cylindrical sample-holder frame mounted rotationally about the vertical axis, light tubes and with a rising laminar air flow cooling the internal face of the samples. The cylindrical frame has solid walls pierced with two rows of apertures to place the samples, and to form suction holes for a secondary air flow.

For the cooling, the instrument comprises an air circulation system with two air flows, with a rising main air column that flows up in the sample-holder cylinder traveling along the internal face of the samples, and a peripheral secondary air flow that strikes the external face of the samples. The secondary make-up air flow comes from a source of cold air. The secondary air flow is created by the suction effect prompted at the holes of the cylinder by the ascent of the main air column. The holes have a variable shuttering system to dose out the peripheral secondary air flow in relation to the rising main air flow.

The drawback of this device lies in the complexity and particularly large spacing requirement of its dual-flow air circulation system. Another drawback is that the testing space of the device and its capacity in terms of numbers of samples is quite restricted when related to the huge space requirement of the cubicle with its air-removal instrumentation at the top, the blower system and the rotational driving system at the lower part, as well as the peripheral air circulation system and the lateral cold air source. This dual-air-flow cooling system also has the drawback of giving rise to substantial temperature differences between the irradiated internal face and the cooled external face of the samples.

German Patent No. 3,243,722 discloses a device that is quite different for the testing of resistance to light and weather changes. This device comprises a large ventilated chamber in which there is positioned a horizontal assembly comprising a ring of light tubes inserted between two horizontal, concentric air conduits and a sample-holder drum mounted rotationally around horizontal conduits. The two conduits are connected to a fan and communicate with each other as well as with the outside of the chamber so that outside air is blown into the first conduit, then returns and is inserted into the space between the first and second conduits to along the light tubes for cooling them while returning to the exterior.

As for the samples positioned on the outer drum, they are cooled separately by another vertical air flow that circulates in a circuit provided with another fan and a cooling exchanger as well as, if necessary, heating means or a heater. This device therefore has two air circulation systems cooling first the samples, and then the light tubes.

In this device, the light tubes as well as a sprinkler system are positioned in conduits that separate them from the samples. This has the drawback of adversely affecting especially the exposure of the samples to light and the efficiency of the system. The device further has the drawback wherein the vertical air flow that crosses the sample-holder drum does not provide a desired cooling of the samples.

SUMMARY OF THE INVENTION

In view of the foregoing background, an object of the present invention to provide a device that exposures samples to radiation to test the ageing thereof, with the samples being subjected to a uniform temperature and a uniform radiation without the above-mentioned drawbacks.

In particular, another object of the present invention is to provide for efficient ventilation of the samples during tests made with the device.

Another object of the present invention is to obtain a device having a reduced number of lamps and a smaller space requirement.

Yet another object of the present invention is to obtain a device having a relatively straightforward design with a high luminous efficiency in relation to the surface of the samples exposed so as to reduce the cost of the tests.

Another object of the present invention is to facilitate the handling of the samples prior to the ageing tests.

Briefly, these and other objects, advantages and features according to the present invention are provided by a device comprising a rotary sample-holder cage whose rotational axis is preferably positioned horizontally, so that the samples are cyclically located in the upper part and then in the lower part of the chamber. This makes it possible to disregard inherent temperature differences, and more essentially, in providing that the device has a swirling air flow around the axis of the cage.

In the present document, the term "swirling air flow" is understood to mean the flow of any mass of air driven by a motion of rotation and convergence about an axis, and by a translation motion directed substantially in this axis. A swirling air flow is characterized also by the gyratory, helical or spiral movement of air about an axis with a speed that is inversely proportional to the distance from the axis.

In the device according to the invention, the air flow enters the periphery of the cage and arrives crosswise to the axis and has components that are tangential and/or radial to the periphery of the cage. The air is then discharged at the center of the cage in parallel to the axis, and has an axial component in the central part of the cage, thus advantageously providing for a symmetry and evenness or regularity of the air flow.

The presence of a swirling air flow can easily be detected by a smoke generator which causes the appearance of a spiral winding of smoke that may rotate several times on the periphery of the cage. This advantageously optimizes generation of heat at the samples before being quickly discharged from the axis of the sample-holder cage. The air flow can thus rotate about a depression for forming a funnel or vortex.

The invention can be obtained with a device that exposures samples to radiation to test their ageing. The device has a chamber comprising a sample-holder cage rotating about an axis, and means for placing at least one electromagnetic radiation lamp in a fixed position and supplying the lamp in the central part of the cage. A particular feature of the device comprises an air circulation system capable of generating a swirling air flow about the axis of the cage. The system comprises fixed air passage apertures positioned around the periphery of the rotary cage and an air passage hole positioned in the axis of the cage.

Preferably, the device comprises an air circulation system with air inlets at the periphery of the cage, and an air removal system in the axis of the cage. The air circulation system preferably comprises fixed air inlet apertures arranged evenly on the periphery of the cage and are rotationally symmetrical about the axis. Each aperture is oriented in a direction contained between the directions that are radial and tangential to the periphery of the cage, and an air removal conduit positioned in the axial prolongation of the central part of the cage. The conduit is oriented in a direction parallel to the axis.

The cage may be mounted rotationally on an axially hollowed-out hub, and the air flow is discharged in the axial hollow of the hub. The air circulation system preferably comprises air suction means positioned in the prolongation of the hollow of the hub. The air circulation system may be an open circuit system, advantageously enabling the direct suction of cool air from the laboratory. As an alternative, the air circulation system can work in a closed circuit.

According to a preferred embodiment of the invention, the cylindrical chamber comprises air inlet louvers positioned on the periphery of the cage. It is advantageously provided that the peripheral air inlet louvers of the chamber will be directed non-radially and that each peripheral air inlet louver will have a depth, an aperture and an angle of tilt with respect to the radial direction such that the radiation of each lamp positioned in the central part of the cage will not cross the inlet hole and will not directly escape from the chamber.

The cage may comprise central elements and peripheral elements extending in the axial direction and are connected by radial elements, the central and peripheral elements extending in a single half space separated by the radial elements. The cage may also comprise circular elements with different diameters enabling the samples to be positioned at different angles of exposure.

The central elements of the cage develop helically about the axis. The cage may be linked to the hub by a disengageable driving mechanism enabling free rotation of the cage. Advantageously, the mechanism comprises means of disengagement in rotation under the effect of a borderline axial torque between the cage and the hub. Advantageously, the mechanism may also comprise means of disengagement or disconnection in translation under the effect of a borderline axial force between the cage and the hub.

According to one alternative embodiment, the device comprises a water tank positioned so as to bath one part of the cage. Finally, according to the invention, the device is designed to work with the axis of the rotary cage positioned in a horizontal direction.

The invention also relates to a method to test the ageing of samples having the particular feature of implementing a device of this kind for exposure to radiation. The method preferably comprises steps placing the samples in a sample-holder cage that rotates about a horizontal axis, and fixedly positioning and supplying at least one electromagnetic radiation lamp positioned on or about the axis of horizontal rotation, and generating a swirling air flow about the horizontal rotation axis. The swirling air flow has, at the periphery of the cage, a rotational motion whose component is included between the tangential direction and the radial direction. The swirling air flow may also have a translation motion at the center of the cage, the component of which is substantially parallel to the axial direction.

The invention can also be obtained with a method for the testing the ageing of samples by subjecting the samples to a vertical rotation about one or more electromagnetic radiation lamps positioned on or about the horizontal rotation axis, and generating a swirling air flow about the rotation axis of the samples. The air flow essentially has components perpendicular to the axis of rotation at the samples.

BRIEF DESCRIPTION OF THE DRAWINGS

Other objects, features and advantages of the present invention shall appear from the following description of an embodiment given purely by way of a non-restrictive example, the description integrating the drawings of which:

FIG. 1A is a cross-sectional schematic side view of the radiation exposure device according to the present invention;

FIG. 1B is a cross-sectional schematic front view of the device according to the present invention;

FIGS. 2B, 2A and 2C are views of an embodiment of the device with a retracted cap according to the present invention. FIG. 2A is a cross-sectional side view without the cap and without the lamp-bearer. FIG. 2B shows the retracted cap in a three-quarter view toward the interior. FIG. 2C shows the kinematic chain of the device as viewed in a cross-sectional rear view along the line C—C of FIG. 2A;

FIGS. 4A and 4B show an axial sectional view and a front view of an advantageous embodiment of a disengageable drive mechanism for a sample-holder cage for the device according to the present invention;

FIG. 5A shows an axial half sectional view and a half profile sectional view of an advantageous embodiment of a disengageable drive mechanism for a sample-holder cage for the device according to the present invention; and FIG. 5B shows a front and a half cross-sectional view of the disengageable drive mechanism illustrated in FIG. 5A.

DETAILED DESCRIPTION OF THE PREFERRED EMBODIMENTS

Figure 3B:
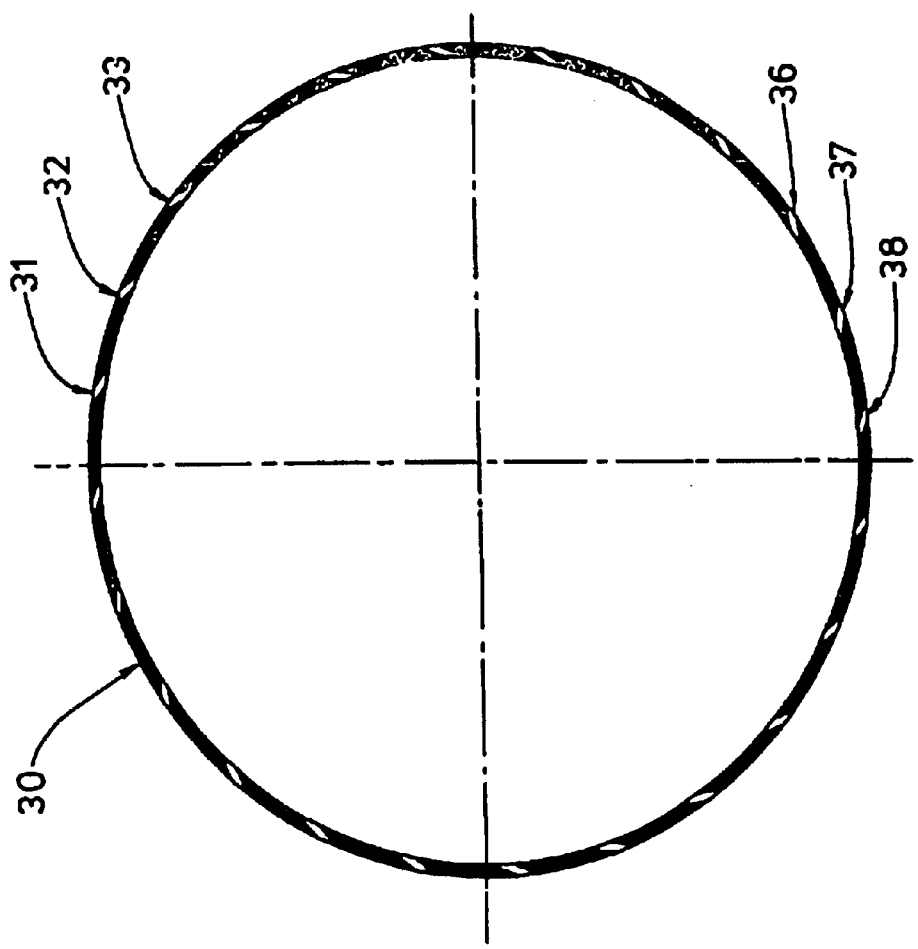
FIGS. 3A and 3B show a profile view and a cross-sectional view of details of an advantageous embodiment of the cap for the device according to the present invention.

In FIGS. 1 to 5, it can clearly be seen that the device is, preferably, generally circular and is rotationally symmetrical about an axis H—H designed to be positioned advantageously in a horizontal direction. In the following description of the embodiment and the operation thereof, it is considered, to simplify matters, that the device is rotationally symmetrical about the axis H—H. Geometries of greater complexity may be planned by those skilled in the art without departing from the framework of the invention.

FIG. 1A thus shows that the device according to the invention comprises a cylindrical and circular chambers 3 and 30. Alternatively, the device may comprise a chamber that is cylindrical but with a section that has a square, rectangular or other form. The chamber has a removable cap 30, preferably shaped like a bowl, that is hermetically fixed to a fixed deck 3. The cage 3, 30 contains a circular sample-holder cage 40 which can be made according to the example of FIGS. 2 and 4, out of a frame of metal rods 41 to 47 arched into the form of circular elements 41, 42, 43, 44, 45 and 46 and curved elements 47 laid out in quarters and joined together.

The cage 40 is fixedly joined by a circular driving piece 49 and a disengageable mechanism 55, 56, 57, 58 and 59 with a hub 50–51. The hub 50–51 is mounted rotationally, possibly on a roller bearing or ball bearing 5, on the deck or decks 2–3 which offer a fixed support. The hub 50 is rotationally driven by a kinematic chain comprising an off-centered motor 20 connected by a gear or chain transmission system 21, 22.

According to the preferred embodiment of the invention, the hub 50–51 is completely hollowed out axially. The hollow portion of the hub 50–51 forms an air flow removal conduit. Similarly, according to the preferred embodiment, the central part of the sample-holder cage 40 is hollowed out, and no rod of the frame appears in the central part of the cage which corresponds to the prolongation of the hollowed-out part of the hub 51.

The invention provides for the fixed positioning of one or more electromagnetic radiation lamps 10 in the central part of the rotating cage 40. The lamp or lamps 10 are connected, namely fixed and electrically powered, directly by an axial part 15 having radial arms 16, 17 in a star-shaped arrangement, to the fixed deck 2, or indirectly by the body 18 of a fan 1.

If only one ultraviolet lamp 10 is fitted into the device according to the invention, it is preferable that the lamp 10, which is generally tube-shaped or is rotationally symmetrical, should be positioned in the central part of the cage. The axis of the lamp is positioned in the axis H—H of the cage. If two or more lamps equip the device according to the invention, it is preferable that the lamps should be positioned symmetrically about the axis of the cage and in parallel to the axis H—H.

In a particularly advantageous way, the arrangement of the lamp or lamps 10 in the central part of the sample-holder 40 on or about the rotation axis H—H enables the samples to be exposed in rotation to a luminous flux that is perfectly homogeneous. This is provided that the samples are positioned in parallel and at the same radial distance from the axis. It is also provided, according to the preferred embodiment of the invention, that the device will comprise air suction means 1 positioned in the prolongation of the hollow portion of the hub 50. It is provided, for example, that a fan 1 will be positioned in the rear prolongation of the hollow portion of the hub 50. The fan 1 may be affixed to the fixed rear deck 2.

Advantageously, the central parts of the cage 40 and of the hub 50, as well as their extended portions are completely unencumbered, except for the lamp-holder 15, so as to allow the free passage of the air flow. Thus, according to the invention, the air flow is discharged in the axial direction H—H to the center of the cage 40. The device advantageously comprises a cage 40 and a hub 50 whose central part is completely hollow.

Furthermore, it is provided in the invention that air inlets 31–38 will be arranged on the periphery of the cage 40. According to the preferred embodiment of the invention, the cylindrical chamber 30 thus comprises louvers 31 to 38, namely air intake apertures, pierced in the cylindrical or near-cylindrical (slightly conical) rim of the cap 30 or more generally of the chamber.

During the tests it is planned to place the samples on the periphery of the cage, and fixedly joining them to the circular elements 41, 42 and 43 of the frame of the cage, especially by using clamps. It is commonly considered that the samples are cut out into plates or boards, generally plane-shaped, so that the samples occupy surfaces that are secant or tangential to the periphery of the circular cage 40, as illustrated in FIG. 1B.

During operation, the samples are therefore in a position where they are tangential or secant to the periphery of the cage 40. The cage is put into rotation and the air suction means 1 start a flow corresponding to an air removal in the axis H—H of the cage 40, the lamp 10 and the hub 50. In a particularly advantageous way, the air heated by the lamp or lamps 10 in the axial position is discharged directly without heating the samples.

The convection heat released by the lamps during operation therefore does not disturb the temperature of the samples during testing. Furthermore, the air removal prompts an air inflow at the periphery of the chamber 30. This air inflow strikes the samples orthogonally or at an angle of incidence with respect to their plane, as illustrated in FIG. 1B. Advantageously, the incidence of the air flow on the samples improves the thermal exchanges.

Contrary to the devices of the prior art, the samples therefore do not have a laminar air flow traveling along them but are subjected to an incident, swirling air flow. In certain embodiments, the air inflow may be strictly radial at the level of the samples placed on the periphery of the cage 40. This case arises especially when each air suction louver 31–38 is formed radially in the cylindrical part of the chamber 30 in assuming that the rotation of the cage 40 does not modify the circulation of air.

In other embodiments, the air inflow at the periphery of the sample-holder cage 40 comprises both a radial component and a tangential component, so that the samples are subjected to an air flow having a certain angle of incidence. In the preferred embodiment, it is thus planned to form non-radial louvers 31 to 38 on the periphery of the cylindrical chamber 30.

Figure 3A:
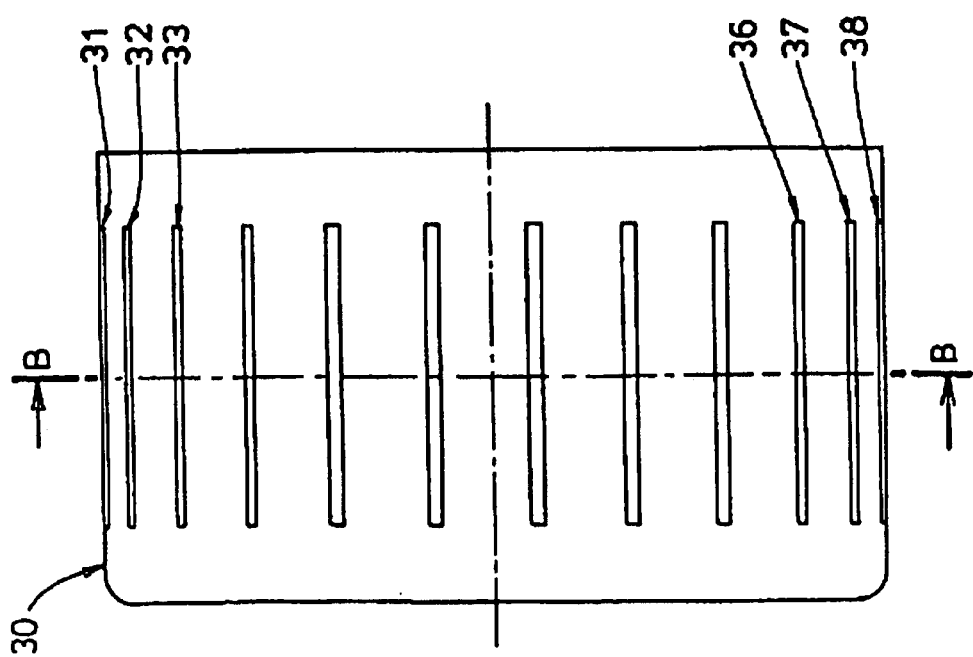

FIGS. 3A and 3B thus show that the quasi-cylindrical rim of the cap 30 of the chamber is notched by fine apertures 31–38 forming axially plotted slots. These slots have the particular feature of penetrating not in a radial plane but obliquely to the radial direction. At the limit, the apertures 31 to 38 may be almost tangential to the cylinder of the cap 30.

In a particularly advantageous way, the oblique holes 31 to 38 enable the air inflow to have tangential and radial components at the level of the samples placed on the periphery of the cage 40. The circulation of air thus prompts a swirling air flow about the axis H—H of the cage 40. The air flow has practically no axial component but only components tangential and/or radial to the periphery of the cage 40, while the air flow has only one axial component H—H at the center of the cage 40.

In the present document, the expression "swirling air flow" covers the borderline case in which the air flow at the periphery of the cage has only a radial component as well as the other borderline case in which the air flow at the periphery of the cage has only a tangential component. The circulation of air is thus advantageously similar to a siphon motion about the axis of the cage, thus providing for optimum thermal exchanges at levels of the samples.

Another essential advantage of the oblique positioning of the air inlet louvers 31 to 38 at the periphery of the cylindrical chamber 30 is that it blocks the direct output of radiation from the lamp 10 while enabling the passage of the air in a manner similar to that of the louver arrangement in a blind or shutter. In the preferred embodiment of the invention, each louver slot 31 has a limited aperture but a sharp angle of tilt with respect to the radial direction as well as a large depth, so that the direct radiation from each lamp 10 positioned in the central part of the cage does not cross the louver 31 and does not escape from the chamber. Furthermore, it is provided optionally, as shown in FIG. 2A, that the cap 30 will comprise a central port 39 made of anti-U.V. glass. This port 39 whose glass cuts off the ultraviolet radiation can be advantageously used to observe the samples during testing, and in preventing harmful radiation from the lamp. Advantageously, the central part of the port 39 may be masked by a central part fixed by radial arms in a star-shaped arrangement (not shown).

The cap 30 is preferably made of sheet metal. It is made by swaging, which gives a slightly conical, near-cylindrical cap. A light embodiment of this kind has the advantage of limiting the cost of the equipment and the investment for the ageing test.

FIGS. 4A and 4B show that the cage 40 is preferably made out of semi-rigid metal wires or rods 41 to 47. The main advantage of such an embodiment is that it limits the weight of the cage 40, hence the size of the driving motor 20. Such an embodiment also facilitates the circulation of air and the handling of the samples. This light embodiment also has the advantage of limiting the cost of the equipment.

In a first simplified embodiment, the cage 40 is formed by circular elements 41, 42 and 43 of identical diameter, fixedly joined by radiating elements 47 arc-shaped as in a basket or a squirrels wheel. The radiating elements 47 simply comprise a portion parallel to the axis to fix the circular elements 41, 42 and 43 and a radial portion to a washer 49 of average diameter, which are fixedly joined to the driving hub 50.

In another embodiment, illustrated in FIGS. 1A and 2A, the cage has several circular elements 41, 42 and 43 and 44—44 having different diameters to be able to position plane samples, either perfectly parallel to the axis by fixing them, for example, to the elements 41, 42 and 43 of the same diameter or obliquely to the axis in fixing them, for example, to the elements 41 and 42 having different diameters. Advantageously, this multiple-position frame provides for the positioning of samples of different lengths at different angles of radiation and at different distances from the light source, thus enabling the exposure of samples of different lengths to the same intensity of illumination.

In the preferred embodiment, shown in FIG. 4, the cage 40 has a particular umbrella-shaped frame. The frame is formed by curved elements 47 positioned in quarters along radial planes so as to radiate around the hollowed-out, central part of the cage 40. As can be seen in FIG. 4A, each curved element 47 has one central portion or element 47' extending in parallel to the axis H—H to the boundary of the hollowed-out central part of the cage 40. The central element 47' is connected to a portion or element 47" extending in the radial direction heading opposite from the center. This radial element 47" is connected or prolonged by a peripheral element 47'" parallel to the axis, which separates the periphery of the cage 40.

This particular feature of the frame of the cage 40 of FIG. 4 is that the central portion 47' and the peripheral portion 47'" of each curved element 47 are located in the same half-space separated by the plane of the radial portions 47'". Each curved element 47 therefore has a hook shape. Subsequently, the circular elements 41, 42, 43 and 44 are fixed, especially by soldering, to the peripheral portions 47'" of the curved elements 47 to form the frame of the circular cage 40. Similarly, small circular elements 45 and 46 may be fixedly joined with the central portions 47' of the curved element 47 to complete the formation of the frame, and advantageously increase the rigidity of the circular cage 40.

Finally, the central portions 47' of the frame of the cage are fixed by fastening pieces, soldering or any other means to a washer-shaped part 49 designed to be fixedly joined to the hub 50. An umbrella-shaped cage frame of this kind can advantageously be used to arrange instruments fixedly within the rotary cage (arrangement not shown). The instruments, which are sensor or actuator type instruments, are attached to the fixed-support deck 3 of the device and project out of the deck (in parallel or obliquely with respect to the axis) to become engaged within the rotary cage 40 without affecting the rotation.

In one example (not shown), a temperature probe is advantageously attached to the deck 3 above the axial lamp 10. The active end of the probe moves forward between the lamp and the samples without preventing the rotation of the cage. In another example (not shown), a water-spraying bank is positioned beneath and parallel to the axial lamp 10 so that it is fixed to the deck 3 to connect it to a water inlet. Advantageously, the bank is thus immobilized within the rotary cage parallel to the plane of the samples, which are then evenly sprayed throughout their surface at each rotation cycle.

Furthermore, according to an improved embodiment (which is not shown) the central portions (47') of the curved elements that extend in the axial direction H—H are not rectilinear, but helically wound about the axis H—H of the cage 40. The advantage of an improvement such as this is that it prevents a sample from being partially placed into the shadow of the central portion of a curved element. The electromagnetic radiation from the central lamp thus uniformly reaches each sample, regardless of its position on the periphery of the cage.

It is also provided, according to one advantageous option that the device according to the invention will comprise a water tank bathing the lower portion of the rotary cage. A half-moon shaped basin (not shown) may thus be fixed to the bottom of the deck 3 of the device. The cage 40 is partially plunged into the water filling the basin.

A device of this kind can be used to test the behavior of the samples in ageing under the combined effect of humidity, water immersion and electromagnetic radiation such as ultraviolet radiation. These factors advantageously cover most of the natural agents of ageing.

Now, from the mechanical viewpoint, the cage 40 is rotationally driven by a kinematic chain 50 comprising particular arrangements as illustrated in FIGS. 2A and 2C. It is advantageously provided that the drive motor 20 will be off-centered instead of being located in the axis H—H of the cage 40. This enables the central hollowed-out central portion of the device and its prolongation to be completely unencumbered, so as not to hamper the circulation of air.

The motor 20 is fixed to a deck 2 with a fixed support. The output pinion 21 of the motor drives a toothed ring 52 fixed to the hub 50–51. The transmission can be done either directly by gear mechanism, the pinion 21 and the toothed ring 52 being in contact, or indirectly by a chain or by a belt 22 tensioned between a pinion 21 and a grooved ring 52, as shown in FIG. 2C, or again by any other transmission means.

In the exemplary embodiment of FIGS. 2A and 5A, the driving ring or plate 52 is attached by screws to a nut 53 stopped on the screw thread of the hub 51. The nut 53 is also used to block a cylindrical spacer 54 against the ring of the ball bearing 5 or the circular rim of the deck 3. Since the other end 55 of the hub is flared, the hub 51 is then rotationally immobilized with respect to the fixed-support deck 3.

Finally, in a particularly advantageous way, it is provided that the cage 40 will be connected to the hub 51 by the disengageable mechanism 50. The hub 50 is thus formed by two concentric bodies 57 and 51 with flared ends 59 and 55, fitted into each other.

As illustrated in FIG. 5A, the body 57 of the hub 50 has a flared funnel shape that ends in a plane circular end 59, with hollowed-out screw threads 58 to attach the cage 40 by a washer 49. The other end of the body 57 of the hub 50, which is cylindrical, has a ring-shaped groove 56 hollowed in it throughout the rim.

Furthermore, the ring-shaped groove 56 has several hemispherical cavities 56' hollowed out in it at several points of its rim without deepening the dip of the groove 56. According to the example of FIG. 5, it is thus planned to position three cavities 56' at an equidistance, at 1200 with respect to one another, on the rim of the ring-shaped groove 56.

In a correlated way, the flared end of the main body 51 of the hub 50 has tubular housings 55 corresponding to the cavities 56' for deepening the groove 56 of the end body 57. Each housing 55 is designed to receive a ball and a spring held by a pressure-setting screw.

When the end body 57 is fitted into the main body 51 of the hub 50, each ball there is engaged in the ring-shaped groove 56, and is then blocked at the bottom of the corresponding hemispherical cavity 56'. Since the balls are kept at the bottom of the cavities 56' hollowed out in the groove 56, this mechanism blocks the body 57 in translation and in rotation with respect to the body 51 of the hub, in a manner similar to what happens during the keying of a plug in a lock cylinder.

However, if excessive torque is exerted to the body 57 as compared with the body 51 of the hub 50, the balls are pushed back out of their respective cavities 56' and the body 57 starts rotating freely about the body 51, with the balls remaining engaged in the ring-shaped groove 56. This mechanism advantageously enables a disengagement in rotation of the cage 40 with respect to the hub 50 when an excessive axial torque appears between the cage and the hub. Advantageously, this disengageable mechanism enables an operator to rotate the cage 40 while the motor 20 is stopped. Similarly, this mechanism prevents the motor 20 from being affected when the cage 40 is accidentally locked in rotation.

Furthermore, this mechanism very advantageously enables uncoupling in translation between the cage 40 and the hub 50 when excessive axial traction is exerted on the cage. By the exertion of traction force on the end body 57 in the axial direction, frontward, the balls finally escape from the bed of the ring-shaped groove 56 and the end body 57 is disconnected from the main body 51 of the hub 50. This mechanism makes it possible to retract or disengage the cage of the device in translation. It is also advantageously provided that each housing 55 will comprise one end reduced to a diameter smaller than that of the balls, to prevent the balls from escaping from the housings 55 when the body 57 gets disconnected.

Other embodiments, alternatives and improvements can by those skilled in the art without departing work of the invention, the object of the ng defined in the following claims.

That which is claimed is:

1. A device for ageing samples being exposed to radiation, the device comprising:
    a sample-holder cage for rotating about an axis thereof;
    at least one electromagnetic radiation lamp;
    a holder for placing said at least one electromagnetic radiation lamp in a fixed position in a central part of said sample-holder cage, and for supplying said at least one electromagnetic radiation lamp with power; and
    an air circulation system for generating a swirling air flow about the axis of said sample-holder cage, said air circulation system having a plurality of fixed air passage apertures around a periphery of said sample-holder cage and an air passage along the axis of said sample-holder cage.

2. A device according to claim 1, wherein said plurality of fixed air passage apertures are evenly arranged around the periphery of said sample-holder cage and are rotationally symmetrical about the axis thereof, each fixed air passage aperture being oriented between directions that are radial and tangential to the periphery of said sample-holder cage, and the air passage conduit being oriented in a direction parallel to the axis of said sample-holder cage.

3. A device according to claim 1, further comprising a hub having an opening therethrough defining the air passage for discharging the swirling air flow; and wherein said sample-holder cage is mounted to said hub.

4. A device according to claim 3, wherein said air circulation system further comprises a fan adjacent the air passage for causing the swirling air flow to discharge.

5. A device according to claim 3, further comprising a disengageable driving mechanism for connecting said sample-holder cage to said hub so that said sample-holder cage rotates therewith.

6. A device according to claim 5, wherein said disengageable driving mechanism disengages rotation of said sample-holder cage based upon an excessive axial torque between said sample-holder cage and said hub.

7. A device according to claim 1, wherein said air circulation system is an open circuit system.

8. A device according to claim 1, wherein each fixed air passage aperture is oriented in a non-radial direction with respect to the axis of said sample-holder cage.

9. A device according to claim 8, wherein each fixed air passage aperture has a depth and an angle of tilt in a radial direction so that radiation from said at least one electromagnetic radiation lamp does not cross each fixed air passage aperture and does not directly escape from said chamber air circulation system.

10. A device according to claim 1, wherein said holder positions said at least one electromagnetic radiation lamp along the axis of said sample-holder cage.

11. A device according to claim 1, wherein said at least one electromagnetic radiation lamp comprises a plurality of electromagnetic radiation lamps; and wherein said holder symmetrically positions said plurality of electromagnetic radiation lamps with respect to the axis of said sample-holder cage.

12. A device according to claim 1, wherein said sample-holder cage comprises:
    a plurality of central elements;
    a plurality of peripheral elements extending in a direction of the axis of said sample-holder cage; and
    a plurality of radial elements connecting said plurality of peripheral elements to said plurality of central elements,
    said plurality of central elements and said plurality of peripheral elements extending in a half space separated by said plurality of radial elements.

13. A device according to claim 1, wherein said sample-holder cage comprises a plurality of spaced apart circular elements, and each circular element having a different diameter for enabling a sample to be positioned at a different angle of exposure.

14. A device according to claim 13, wherein each circular element is helically configured along the axis of said sample-holder cage.

15. A device according to claim 1, further comprising a water tank adjacent said sample-holder cage for bathing at least a portion thereof when said sample-holder cage is rotating.

16. A device according to claim 1, wherein the axis of said sample-holder cage is in a horizontal direction.

17. A device according to claim 1, wherein said at least one electromagnetic radiation lamp comprises a mercury vapor lamp.

18. A method for ageing samples comprising:
    placing at least one sample within a sample-holder cage;
    rotating the sample-holder cage about an axis thereof;
    exposing the at least one sample to radiation from at least one electromagnetic radiation lamp placed in a fixed position in a central part of the sample-holder cage;
    generating a swirling air flow about the axis of the sample-holder cage using an air circulation system having a plurality of fixed air passage apertures around a periphery of the sample-holder cage, and an air passage along the axis of the sample-holder cage.

19. A method according to claim 18, wherein the swirling air flow has, at the periphery of the sample-holder cage, a rotational motion whose component is included between a tangential direction and a radial direction, and the swirling air flow has a translation motion at a center of the sample-holder cage, a component of which is substantially parallel to the axis of the sample-holder cage.

20. A method according to claim 18, wherein the plurality of fixed air passage apertures are evenly arranged around the periphery of the sample-holder cage and are rotationally symmetrical about the axis thereof, each fixed air passage aperture being oriented between directions that are radial and tangential to the periphery of the sample-holder cage, and the air passage conduit being oriented in a direction parallel to the axis of the sample-holder cage.

21. A method according to claim 18, further comprising a hub having an opening therethrough defining the air passage for discharging the swirling air flow; and wherein the sample-holder cage is mounted to the hub for rotation therewith.

22. A method according to claim 21, further comprising a driving mechanism for connecting the sample-holder cage to the hub; and further comprising disengaging the driving mechanism based upon an excessive axial torque between the sample-holder cage and the hub.

23. A method according to claim 18, wherein each fixed air passage aperture is oriented in a non-radial direction with respect to the axis of the sample-holder cage.

24. A method according to claim 23, wherein each fixed air passage aperture has a depth and an angle of tilt in a radial direction so that radiation from the at least one electromagnetic radiation lamp does not cross each fixed air passage aperture and does not directly escape the air circulation system.

25. A method according to claim 18, wherein the at least one electromagnetic radiation lamp is positioned along the axis of the sample-holder cage.

26. A method according to claim 18, wherein the at least one electromagnetic radiation lamp comprises a plurality of electromagnetic radiation lamps; and wherein the plurality of electromagnetic radiation lamps are positioned with respect to the axis of the sample-holder cage.

27. A method according to claim 18, wherein the sample-holder cage comprises:

a plurality of central elements;

a plurality of peripheral elements extending in a direction of the axis of the sample-holder cage; and a plurality of radial elements connecting the plurality of peripheral elements to the plurality of central elements, the plurality of central elements and the plurality of peripheral elements extending in a half space separated by the plurality of radial elements.

28. A method according to claim 18, wherein the sample-holder cage comprises a plurality of spaced apart circular elements, each circular element having a different diameter for enabling a sample to be positioned at a different angle of exposure.

29. A method according to claim 28, wherein each circular element is helically configured about the axis of the sample-holder cage.

30. A method according to claim 18, further comprising bathing at least a portion of the sample-holder cage when rotating.

* * * * *